United States Patent
Tayot et al.

(10) Patent No.: US 10,456,500 B2
(45) Date of Patent: Oct. 29, 2019

(54) IMPLANTABLE PREPARATIONS FOR REGENERATION OF TISSUES AND TREATMENT OF WOUNDS, THEIR METHOD OF PREPARATION, AND METHOD OF TREATMENT OF PATIENTS WITH SAID IMPLANTABLE PREPARATIONS

(71) Applicant: Khorionyx, La Tour de Salvagny (FR)

(72) Inventors: Jean-Louis Tayot, La Tour de Salvagny (FR); Jean Bernasconi, Sommieres (FR)

(73) Assignee: KHORIONYX, La Tour de Salvagny (FR)

( * ) Notice: Subject to any disclaimer, the term of this patent is extended or adjusted under 35 U.S.C. 154(b) by 305 days.

(21) Appl. No.: 14/778,183

(22) PCT Filed: Mar. 18, 2014

(86) PCT No.: PCT/EP2014/055449
§ 371 (c)(1),
(2) Date: Sep. 18, 2015

(87) PCT Pub. No.: WO2014/147092
PCT Pub. Date: Sep. 25, 2014

(65) Prior Publication Data
US 2016/0279293 A1    Sep. 29, 2016

(30) Foreign Application Priority Data

Mar. 18, 2013  (EP) .................................... 13305318

(51) Int. Cl.
| | | |
|---|---|---|
| *A61L 27/36* | (2006.01) | |
| *A61L 27/58* | (2006.01) | |
| *A61L 27/22* | (2006.01) | |
| *A61K 38/42* | (2006.01) | |
| *A61Q 19/08* | (2006.01) | |
| *A61K 8/98* | (2006.01) | |
| *A61K 8/64* | (2006.01) | |
| *A61K 35/16* | (2015.01) | |
| *A61L 27/54* | (2006.01) | |
| *A61K 45/06* | (2006.01) | |

(52) U.S. Cl.
CPC ............ *A61L 27/3616* (2013.01); *A61K 8/64* (2013.01); *A61K 8/981* (2013.01); *A61K 8/983* (2013.01); *A61K 35/16* (2013.01); *A61K 38/42* (2013.01); *A61K 45/06* (2013.01); *A61L 27/227* (2013.01); *A61L 27/3612* (2013.01); *A61L 27/54* (2013.01); *A61L 27/58* (2013.01); *A61Q 19/08* (2013.01); *A61K 2800/592* (2013.01); *A61K 2800/91* (2013.01); *A61L 2300/412* (2013.01); *A61L 2300/414* (2013.01); *A61L 2300/45* (2013.01); *A61L 2300/604* (2013.01); *A61L 2300/64* (2013.01); *A61L 2400/06* (2013.01); *A61L 2430/34* (2013.01); *A61M 2202/0021* (2013.01)

(58) Field of Classification Search
None
See application file for complete search history.

(56) References Cited

U.S. PATENT DOCUMENTS

| | | | |
|---|---|---|---|
| 6,949,625 B2 * | 9/2005 | Tayot | A61K 38/39 530/356 |
| 7,709,017 B2 | 5/2010 | Tayot et al. | |
| 2004/0248774 A1 | 12/2004 | Tayot | |
| 2009/0074736 A1 * | 3/2009 | Tayot | A61K 9/0024 424/93.71 |
| 2009/0312239 A1 | 12/2009 | Tayot et al. | |
| 2012/0183501 A1 | 7/2012 | Tayot et al. | |
| 2015/0011003 A1 * | 1/2015 | Kuriyama | C12N 5/0663 435/377 |

FOREIGN PATENT DOCUMENTS

| | | |
|---|---|---|
| WO | WO-2010/100570 | 9/2010 |
| WO | WO-2014/147092 | 9/2014 |

OTHER PUBLICATIONS

Varghese (Effects of Serum From Children with Newly Diagnosed Crohn Disease on Primary Cultures of Rat Osteoblasts, 2002).*
International Search Report for PCT/EP2014/055449 dated May 14, 2014.
Jun Araki et al: "Optimized Preparation Method of Platelet-Concentrated Plasma and Noncoagulating Platelet-Derived Factor Concentrates: Maximization of Platelet Concentration and Removal of Fibrinogen", Tissue Engineering Part C: Methods, vol. 18, No. 3, (Mar. 1, 2012), pp. 176-185.
Scalfani, Anthony P et al: "Induciton of Dermal Collagenesis, Angiogenesis, and Adipogenesis in Human Skin by Injection of Platelet-Rich Fibrin Matrix", Arch Facial Plast Surg, (Oct. 17, 2011), pp. E1-E5.
Fernandez-Cossio Sergio et al: "Biocompatibility of Two Novel Dermal Fillers: Histological Evaluation of Implants of a Hyaluronic Acid Filler and a Polyacrylamide Filler", Plastic and Reconstructive Surgery, (May 2006), pp. 1789-1796.
Ayache et al: "Fernandez-Cossio Sergio et al: Comparison of proteomic profiles of serum, plasma, and modified media supplements used for cell culture and expansion", Journal of Translational Medicine, vol. 4, No. 40 (2006), pp. 1-8.

* cited by examiner

*Primary Examiner* — Nghi V Nguyen
(74) *Attorney, Agent, or Firm* — B. Aaron Schulman, Esq.; Stites & Harbison, PLLC (57) ABSTRACT

A new preparation for regenerating tissues or healing wounds, which can be administered to a patient, which comprises serum and globin being insoluble at physiological pH, said preparation being obtained by adding said serum to said globin being insoluble at physiological pH.

6 Claims, 5 Drawing Sheets

IMPLANTABLE PREPARATIONS FOR REGENERATION OF TISSUES AND TREATMENT OF WOUNDS, THEIR METHOD OF PREPARATION, AND METHOD OF TREATMENT OF PATIENTS WITH SAID IMPLANTABLE PREPARATIONS

FIELD OF THE INVENTION

Implantable preparations for regeneration of tissues and treatment of wounds, their method of preparation, and method of treatment of patients with said implantable preparations The present invention relates to new preparations which can be administered to animals and humans, including for regeneration of tissues and treatment of wounds.

It also relates to a method of manufacturing these preparations from blood, including from autologous blood for humans.

It also relates to a method of treatment of animals and humans by administering these preparations.

BACKGROUND OF THE INVENTION

In the field of regenerative medicine, either for therapeutic purposes or for plastic surgery, including skin wrinkles treatment, the principle of in situ administration of cell growth factors, mainly platelets or platelet derived growth factors is now of use.

It was already suggested to add such factors to tissue filling or augmentation or regeneration or wound healing implantable preparations, such as hyaluronic acid preparations, collagen preparations, globin and other organic material preparations, ceramics, and synthetic polymers, including polylactide and polylactide glycolide polymers.

The U.S. Pat. No. 6,949,625 discloses an implantable, including injectable tissue filling, augmentation and healing preparation comprising globin being insoluble at physiological pH, preferably homologous, and more preferably autologous globin, which preparations can optionally comprise healing products or cell growth products, or cells.

The U.S. Pat. No. 7,709,017 discloses preparations which are obtainable from soluble globin or globin derivatives, and which can optionally comprise healing products or BMP type growth factors.

The US patent application 20090312239 discloses preparations of globin being insoluble at physiological pH, which can comprise adhesive, filling, augmentation or healing agents.

The US patent application 20120183501 discloses a new healing method comprising the step of administering to the patient, in need thereof, a preparation of globin being insoluble at physiological pH, which preparation may further comprise platelets, or PDGF type growth factors derived from the platelets of platelet rich plasma (PRP), or recombinant products, or cell growth factors (EGF, FGF, . . . ).

In these preparations, the globin component, being insoluble at physiological pH, was prepared by methods such as separating erythrocytes from the whole blood, inducing the hemolysis of the erythrocytes and submitting the hemoglobin to a heme separation step, the erythrocytes being obtained, for example from blood transfusion pouches, or being separated from a donor blood sample, preferably from the patient.

The US patent application 20090074736 discloses a preparation of globin being insoluble at physiological pH, obtained by submitting the whole blood comprising the erythrocytes and the plasma to a depigmentation step in a medium, such as an acetone containing medium, that extracts or dissolves the heme but leaves, in a substantially undissolved state, the globin and the other constituents of proteinic nature submitted to its action, including albumin, alpha- beta- and gamma-globulins, but also blood clotting factors, as well as the platelet factors in the embodiment where the platelets were not initially separated from the blood for further addition to the globin preparation. According to the application 20090074736, all the blood proteins, the platelets and other cells, are submitted to the acetone process which may induce some denaturation of particular proteins and cannot guarantee that they will keep their original structure in the final preparation.

The state of the art in using blood components for tissue regeneration is well summarized in a recent paper published by Jun Araki et al: 2012[1]. A copy of the full introduction of this paper, with the included scientific references is here below reproduced:

""The preparation of platelet-rich plasma (PRP) was originally developed as a method to divide red blood cells (RBCs) and plasma from whole blood (WB) in blood transfusion hematology[2]. PRP was first used for hemostasis during surgical operations and platelet transfusions for some thrombocytopenic disorders[3]. It was revealed through a number of studies that various bioactive substances including platelet-derived growth factor (PDGF), transforming growth factor-beta (TGF-b) and epidermal growth factor (EGF), were discharged from the alpha granules of platelets into plasma when platelets were destroyed and activated[4-5]. These growth factors are contained in wound exudates from injured subcutaneous tissue and are important in the early phase of the wound healing process[6]. Specifically, they promote stromal stem cell proliferation and angiogenesis and are regarded as key signals in tissue repair/regeneration[7-9].

Autologous PRP has less safety concerns than cell-based regenerative therapies. As such, PRP is an issue of extensive research for tissue engineering and regenerative medicine[10-11]. PRP has been therapeutically used to accelerate wound healing and tissue repair in dentistry since 1998[12], and the clinical application of PRP was recently expanded to other fields, including cardiac surgery[13], ophthalmology[14], oral and maxillofacial surgery[15], orthopedic surgery[16], plastic surgery[17-18], sports medicine[19] and cosmetic medicine[20-21]. For therapeutic purposes, PRP extracted from WB through a single centrifugation is frequently concentrated by a second centrifugation. The first centrifugation is slow to avoid spinning down the platelets, whereas the second spin is fast, so the platelets are spun down. In this study, we refer to this concentrated PRP by the second spin as platelet-concentrated plasma (PCP) to differentiate it from PRP.

Despite the increasing use of PRP or PCP therapeutically, its reported clinical effects are quite variable[22]. In fact, there is even a report that concludes that it is invalid[23]. Although many commercialized devices are now available for the clinical preparation of PRP/PCP, there is no standardized protocol for PRP/PCP preparation. Moreover, there have been surprisingly few scientific studies on how to optimize the preparation of human PRP/PCP. For example, there has not been a comprehensive study on how the centrifugal force exerted on WB contained in common laboratory ware affects PRP/PCP yield. There are many reasons for a lack of such studies besides the obvious difficulty of obtaining sufficient quantities of fresh human WB samples. One of the many reasons is the complexity of blood coagulation (fibrin polymerisation) and platelet aggregation. Since the precise and consistent control of fibrinogen and platelets is very difficult, well-designed studies are hard to plan and implement. Another reason is that the evaluation methods for the PRP/PCP products[24-25] have not been consistent among previous studies. Finally blood components and physical properties vary between patient samples, making standardization difficult.""

This introduction ends with the description of the goal of the authors which is to publish a better standardized centrifugation process to prepare PRP and PCP. This technique is complex, time consuming and must be carried out by the doctor or his assistant. At the end of the process, there is no guarantee that PRP will remain sterile, unless working in a specific environment which is rarely available to the doctor or his assistant. Because of the presence of platelets, a final sterilization of PRP through filtration membranes is not possible.

A. P. Sclafani, S. A Mc Cormick: 2011[26] introduce their paper with the following statement:

""Since the time of Pare, modern surgical care has relied on optimization of local tissue conditions to allow wounds to heal unimpeded. With an improved understanding of the effects of local growth factors, surgeons have begun to manipulate the wound environment to promote more rapid and effective healing. Isolated growth factors have been applied with some success topically (becaplermin for diabetic foot ulcers and palifermin for radiation induced mucositis), but platelet-rich plasma (PRP) has been promoted in the last decade as a more natural and more potent method of manipulating wound healing. However the process can be time consuming and the results equivocal[27-28].""

Then they describe their experience with PRFM (platelet-rich fibrin matrix). PRFM must be prepared from PRP by the surgeon or his assistant with a kit, under the trade name "Selphyl". A sterile manipulation from blood sampling to the final injection is facilitated by the kit, but requires rigorous attention. It takes half an hour. In the clinical use of PRP, fibrinogen in the PRP frequently leads to uncontrollable coagulation and platelet activation. Although fibrin gel may be useful as a controlled-release carrier of growth factors[29] or as a filler injectable[30], the formed fibrin gel is quickly degraded by the physiological fibrinolysis caused by tissue plasminogen activators, at the origin of the release of plasmin being responsible for the enzymatic cleavage of the fibrin network. The globin implant is not sensitive to the fibrinolysis reaction and is surprisingly more resistant than any other blood protein to the local biodegradation, probably because of its insoluble character and its very high local concentration. Also, the formed fibrin gel reduces the final product volume, hinders the easy injection of PRP, and is not preferable in many clinical situations. In any case, activated PRP or PRFM must be injected within few minutes to avoid full coagulation of the calcium containing plasma into the syringe, limiting the time for injection or preventing injection even through large needles. Different kits are commercially available and require the same obligations.

The reference papers cited above by Jun Araki et al: (2012) and A. P. Sclafani, S. A Mc Cormick: (2011) are believed to be representative of the state of the art for tissue regeneration. All describe PRP or derived products for tissue regeneration as the only used blood component for practical use. PRP is a liquid and before its injection it must be "activated" by addition of thrombin and/or calcium cations ($Ca^{++}$) to generate a solid gel, in order to stick on the wound or/and delay the local diffusion of soluble growth factors and other active soluble components. This solidification of PRP is made possible by activation of fibrinogen and other coagulating factors present in plasma or PRP by thrombin and/or Ca++ addition.

BRIEF SUMMARY OF THE INVENTION

The present invention proposes to provide new preparations which overcome these drawbacks and allow delivering platelet derived factors in a more reliable way, in order to improve the regeneration of tissues and the treatment of wounds. A further aim of the present invention is to allow such preparations to be completely autologous. Another aim is to provide such preparations which have an important tissue filling or augmentation effect from the start. Still a further aim of the present invention is to easily prepare sterile preparations. A further aim is also to provide such preparations which are easier to prepare, to store, and to deliver. Finally another aim is to avoid any specific preparation by the doctor or his assistant.

DETAILED DESCRIPTION OF EXEMPLARY EMBODIMENTS

An object of the present invention is a new preparation which can be administered to a patient, which comprises serum, and preferably autologous serum, and globin being insoluble at physiological pH. Said preparation is obtained by adding said serum to said globin being insoluble at physiological pH. The globin may be obtained from the erythrocytes after their separation from the plasma or from the serum.

Preferably this new preparation is a preparation for use in a therapeutic method of regenerating tissue, including for filling wrinkles, or other cutaneous flaws, and/or for augmentation of tissues, including deficient sphincters, vocal cords, periodontal tissues, plastic or cosmetic surgery for the augmentation of lips, cheeks, or other body parts, alone or in association or mixture with other augmentation materials, and/or for healing of internal surgical wounds, of parts of organs, of chronic wounds of cutaneous tissues, including in diabetic patients or patients affected by arterial or venous disorders which create poor local vascularization of the limbs, or in patients affected by scars, and/or for aiding the regeneration of a granulation tissue on deep burn wounds after excision of the necrotic tissues.

While it is possible for the serum in said preparation to be diluted in an aqueous vehicle or, on the contrary, more concentrated with regard to the native serum, it is preferred for the serum component in the preparation to be at a concentration between 10% and 120% of the patient's native serum, and more preferably to be substantially at the same concentration.

It is preferred for said preparation to be implantable, which means that it can be administered in or on a tissue of the patient in need thereof, by parenteral injection, or by implantation, or by deposition on an open tissue, for example a wound, and to remain present for substantial time.

In the present invention serum means the liquid part of a blood sample, once clotted.

It is preferred that the globin is homologous globin, i.e. from the same species, and for humans it is even more preferred that the globin is autologous globin, i.e. prepared from a blood sample of the same patient.

In the most preferred embodiment, both components, namely the serum and the globin, are obtained from the same blood sample of the patient.

These implantable soluble or insoluble globin preparations are preferably in the form of pastes or gels, or solid materials like powder, granules, dressings, or films, or even shaped implants.

Although the respective volume proportions of globin to serum can widely vary, it is preferred that, at least in pasty or gel forms, the proportions of globin/serum (weight of globin per weight of paste) is preferably of at least 14%, more preferably at least 15%, and even more preferably at least 18% and even 20%, while the pasty preparation can still be delivered through the thinnest injection needles.

The preparations according to the present invention can optionally comprise other components, including:
  tissue filling or augmentation materials, for example collagen, gelatin, cross-linked hyaluronic acid, synthetic filler polymers, ceramic particles, hydroxy apatite, bone particles. If such materials are present it is preferred that their proportion is lower than the globin proportion;
  wound agents, including healing polymeric agents for example oxidized cellulose;
  adhesive agent selected among synthetic or natural adhesive polymeric agents;
  hemoglobin, preferably autologous hemoglobin;
  other cell growth factors; and/or
  cells, including stem cells, blasts, such as fibroblasts, osteoblasts, chondroblasts, or differentiated cells such as fibrocytes, osteocytes, chondrocytes, adipocytes.

The cells can be cultured cells or isolated cells, but it is also possible to add to the preparation according to the invention autologous tissues, for example bone tissues or fat tissues obtained from the patient and treated as usual for autografts, for example homogenized or comminuted.

Another object of the invention is a method for manufacturing a preparation according to the invention, comprising the steps of,
  obtaining a whole blood without any anticoagulant agent
  allowing said whole blood sample to clot,
  separating the obtained serum from said clot,
  optionally submitting an amount of said serum to a test for infectious disease markers,
  adding said serum to a preparation containing globin being insoluble at physiological pH.

It is preferred that the serum is homologous serum, i.e. obtained from blood of the same species as the animal to be treated, and it is far more preferred, especially for humans, that the serum is autologous serum, i.e. obtained from the patient's blood.

It is also preferred for the globin component to be homologous globin and it is more preferred, especially for humans, that the globin is autologous.

Preferably both serum and globin are homologous, more preferably with the serum being autologous, and most preferably for both serum and globin to be both autologous.

The globin component can be prepared, for example, according to the methods disclosed in the U.S. Pat. Nos. 6,949,625; 7,709,017; 20090312239; 20120183501; which are herein incorporated by reference and to which the person skilled in the art may refer.

But it is preferred to prepare the globin component from a blood clot, preferably an autologous blood clot.

Globin can also be obtained from erythrocytes after their separation from the plasma of the blood.

In one embodiment, the method comprises the following steps,
  first allowing the sterile whole blood, devoid of anticoagulant agent, to clot,
  withdrawing the serum
  optionally washing the clot with physiological saline,
  adding sterile water and stirring or otherwise homogenizing to dissociate the clot and release the hemoglobin,
  clarifying the hemoglobin, for example by one centrifugation step,
  preferably oxidizing the hemoglobin to methemoglobin, preferably by adding sodium nitrite,
  extracting the heme part from the hemoglobin, by an acetone containing agent, preferably at acidic pH,
  separating the precipitated globin from the liquid, preferably by a filtration step,
  dissolving the precipitated globin under acidic pH in sterile water,
  adjusting the pH to neutral, which precipitates the globin,
  optionally washing the precipitate,
  recovering the pasty globin,
  optionally drying the globin.

As the globin component of the preparation can easily be obtained in a sterile form, just by preparing it in a sterile environment, and the serum component can easily be submitted to a sterile filtration step, one can directly obtain a sterile preparation, which is ready for use.

The pasty globin, or the dry globin powder can then be mixed to the serum, to form a preparation according to the invention, or they can be stored separately and mixed later.

According to the preferred embodiment of the invention, this method for obtaining globin can use the same blood clot from which the serum was separated, which allows to prepare both serum and globin components from the same whole blood, for example a 20 mL blood sample, from the patient himself.

Another object of the present invention is a method of regenerating tissues, comprising the step of administering to a patient in need thereof, an efficient amount of a preparation according to the present invention, in or on his tissue to be regenerated.

Preferably said preparation is implanted in or on the tissue.

In one embodiment this method is a method for filling wrinkles, or other cutaneous flaws. One uses the preparation in a pasty form able to be injected through the thinnest injection needles, where the concentration of globin in the preparation is preferably at least 12%, and more preferably higher.

In another embodiment, the invention provides a method for augmentation of tissues, for example deficient sphincters, periodontal tissues, or for plastic or cosmetic surgery, for the augmentation of lips, cheeks, or other body parts, alone or in association or mixture with other augmentation materials, for example autologous adipose tissue. In these applications it is preferred to use the preparation in pasty form, preferably by injection.

In another embodiment the invention provides a method for healing of internal surgical wounds, of parts of organs, of chronic wounds of cutaneous tissues, for example in diabetic patients or patients affected by arterial or venous disorders which create poor local vascularization of the limbs, or in patients affected by scars.

In another embodiment the preparations can also be used for aiding the regeneration of a granulation tissue on deep burn wounds after excision of the necrotic tissues. This step is important prior to the grafting of sheets of epithelium cultivated in vitro The present invention thus allows using autologous serum and does not need to use autologous plasma derived products. The preparations according to the present invention secure a high content in growth factors, higher than plasma derived products[31], which may be decisive when it comes to regenerative properties. It allows guaranteeing the sterility of the final preparation in a simple way. A final sterilization of serum is made possible by membrane filtration, because of the absence of platelets. Further the preparations according to the invention can be stored for long time, due to the excellent stability of the globin component and of the serum component, contrary to platelets containing liquids or fibrin based gels. Serum is stable for few days at +4° C. and may be stored for several years in the frozen state, until thawing it for its final use.

Contrary to plasma, the serum alone cannot be solidified any more, due to the absence of any active component of the coagulation system. The serum is definitively a liquid which would diffuse immediately out of the injection site. All attempts to mix serum and collagen particles were not successful. Sterile collagen particles or gels do not swell in a reasonable time, when mixed with serum at physiological pH. The resulting mixture, even after hours of incubation is not homogeneous and cannot be injected with reasonable needle sizes. Other hydrophilic polymers like hyaluronic acid based particles or gels may swell in contact with serum. However their use for tissue regeneration is not preferred because their electronegative properties repulse cells which cannot attach, grow and differentiate to recreate a new tissue[32]. Surprisingly mixing the autologous serum with insoluble globin powder makes possible to prepare very high concentrations of paste, from 15 to 20 percent (weight of globin per weight of paste). Such high concentrations of globin, equal to or above 15%, cannot be prepared according to the U.S. Pat. No. 6,949,625 of Tayot, and in any case could not been reliably injected through thin hypodermic (30 g) needles. This new mixture of serum and globin between 15 to 20 percent ("seroglobin") can be prepared in sterile conditions under a laminar air flow. It can also be distributed in syringes which can be stored in a freezer and then thawed later on, even after years, before use. The doctor or surgeon may use them immediately without any intermediate task. Surprisingly, even after freezing and thawing, the seroglobin paste is easily injected through the thinnest hypodermic needles despite its high concentration and may be used as dermal filler or in regenerative medicine applications.

Further the present invention allows keeping the "autologous" status of the final mixture of serum with its additive. Autologous means that all components of the injectable material come from the patient himself, without any foreign additive. This is very important for safety considerations, for acceptance by the patient and also for facilitating the regulatory approval of this new biomaterial. Serum for instance is the natural liquid product easily separated from the coagulated blood, without any additive. On the contrary PRP, which is also autologous, must be mixed with calcium salts or/and thrombin, foreign to the patient, before being used. So, the PRP derived product which is injected is not entirely autologous in this respect and this may create more complex problems for its regulatory approval. It was found that globin is the only additive which can be prepared from the blood of the same patient to confer highly viscous properties to the resulting mixture with serum. No impurities, no other component than globin is present in the globin powder. So, the globin powder may really be considered as an autologous product, when it is prepared from the blood of the patient himself. This is exemplified in example 2 in which serum is prepared from a first blood sample and globin is prepared from a second blood sample.

According to a preferred embodiment of the same present invention it is also surprisingly possible to mix the serum from the patient with the globin prepared from an unrelated donor. Contrary to serum which contains undesirable antibodies for recipients of another blood type, globin does not contain antibodies or infectious agents and may be used safely on other recipients.

In another aspect of our invention we have discovered that we can prepare the serum and the globin from the same coagulated blood sample. So far, all processes to prepare globin started from blood collected with anticoagulant additives, like sodium citrate, EDTA or heparin. This was known as the easiest way to separate the red cells from plasma by centrifugation steps and then preparing purified hemoglobin by hemolysis of red cells in water. Surprisingly, it is possible to prepare globin of high purity starting from the clot of blood cells and fibrin which may also contain other blood proteins. In such a case, the serum is directly available from the supernatant fraction of the coagulated blood. The globin may then be extracted from the red clot after washing it by a saline solution. An example of this method is disclosed in Example 3. At the end of the process, the respective quantities of serum and globin powder prepared from one single blood sample enable to prepare the right concentration of the "seroglobin" paste equal to or above 15%. This is an important advantage for the patient, because it allows dividing the quantity of blood drawn from the patient by a two fold factor, for example 20 mL instead of 40 mL as shown in examples 2 and 3.

BRIEF DESCRIPTION OF THE DRAWING FIGURE

The following examples illustrate, in a non limiting manner, embodiments of the invention, in relation with the drawing comprising.

EXAMPLE 1: PREPARATION OF AUTOLOGOUS SERUM FROM COAGULATED BLOOD mL of human blood are drawn from a patient by venous puncture and collected in five dry Vacutainer® tubes without any anticoagulant agent. The tubes are stored at room temperature for 30 minutes until coagulation of the blood and are then stored at +4° C. After one day or more, pour the content of all blood tubes into a 100 mL pot. Collect the serum with a 25 mL sterile pipette and introduce it into a 20 mL luer syringe. Connect the 20 mL syringe to a sterile syringe filter equipped with a 0.2 µm membrane. Filter the serum solution and collect around 11 mL of sterile serum into another 20 mL sterile syringe. Close the serum syringe with its cap and store it momentarily at +4° C. until its use.

EXAMPLE 2: PREPARATION OF AUTOLOGOUS HUMAN GLOBIN POWDER FROM ANOTHER BLOOD SAMPLE OF THE SAME PATIENT 20 mL of human blood are drawn from a patient by venous puncture and collected in five EDTA or citrate containing Vacutainer® tubes. The tubes are then kept at +4° C. and may be stored for two weeks. The blood is introduced into two 50 mL centrifugation buckets and diluted with physiological saline solution. After centrifugation at 2000 rpm for 3 minutes, the supernatant plasma is rejected and replaced by new saline solution. After two washings, red cell pellets are gathered and completed with 30 mL of water to induce the hemolysis. Complete the hemolysis during 5 minutes. Transfer the hemoglobin suspension into one centrifugation bucket. Clarify the hemoglobin solution by one centrifugation step at 3000 rpm for 10 mn at +20° C. 0.9 mL of 1M glycine and then 0.45 mL of 1M sodium nitrite are added to the clarified hemoglobin solution. After oxidation of the hemoglobin to methemoglobin, the red colour of hemoglobin turns black. The solution of oxidized blood is then added drop by drop, with vigorous stirring, to 500 ml of acetone containing 5 mL of 12N concentrated hydrochloric acid. The black pigment of the heme is extracted in acetone, while the whitish globin is immediately precipitated with all residual blood proteins. The suspension is then filtered through a rectangular textile filtration membrane having a porosity of about 1 micron, which is rolled up along its length to form a tube, the two sides of which are bonded together (for example: tubes having an inside diameter of 20 mm, bonded by ultrasound, made of SEFAR NITEX 03-1/1 fabric. One end of the tube is connected to a funnel for introducing the suspension to be filtered, while the other end is closed off by a clip. The globin precipitate accumulates in the tube, while the pigmented acetone solution is readily filtered and can be removed into a retention container before being evacuated for recycling of the acetone. At the end of the filtration, the acid precipitate is resuspended in 200 ml of acetone and then filtered again through the same tube in order to remove residual traces of pigments. The acid globin precipitate is then dissolved in 100 mL of distilled sterile water, and the solution is filtered through sterile 0.45 µm or/and 0.2 µm porous membranes. The acidic pH (=2.5) is adjusted at a neutral value (pH 7.0±0.2) by addition of NaOH 1N. The globin precipitates heavily, while any other residual protein remains soluble in the supernatant. The neutral precipitate of purified globin is washed on the same filtration mesh as before. Finally the insoluble globin paste is washed by acetone to remove its water content and then dried by an air flow or under vacuum to prepare a neutral insoluble globin powder. The globin powder weighs 2.05 grams and is distributed in 5 mL luer syringes (500 mg per syringe). The residual quantity of powder is used to test its sterility by inoculation into a culture medium. This powder may be directly sterile if prepared under a laminar air flow. If necessary, the insoluble globin powder may be sterilized by beta or gamma irradiation at a dose of 5 to 30 kGray.

EXAMPLE 3: PREPARATION OF AUTOLOGOUS HUMAN GLOBIN POWDER FROM THE SAME COAGULATED BLOOD USED FOR SERUM PREPARATION

The example 1 is continued by the following operations, which means that no other blood sample is required, contrary to the example 2. The blood clots left after serum removal are washed by a sterile physiological saline solution (9 g/L NaCl solution). Incubate for 2 mn with gentle agitation and remove the washing saline with a pipette. Fill the pot again with saline and repeat the same operation 3 times. Introduce the clots into one 30 mL syringe. Fill the syringe with about 20 mL sterile water. Dissociate the clots and homogenize the content of the syringe by transfer of its content into another 30 mL syringe through a coupler. Complete the hemolysis during 5 minutes and proceed exactly as in the example 2.

Figure 1:
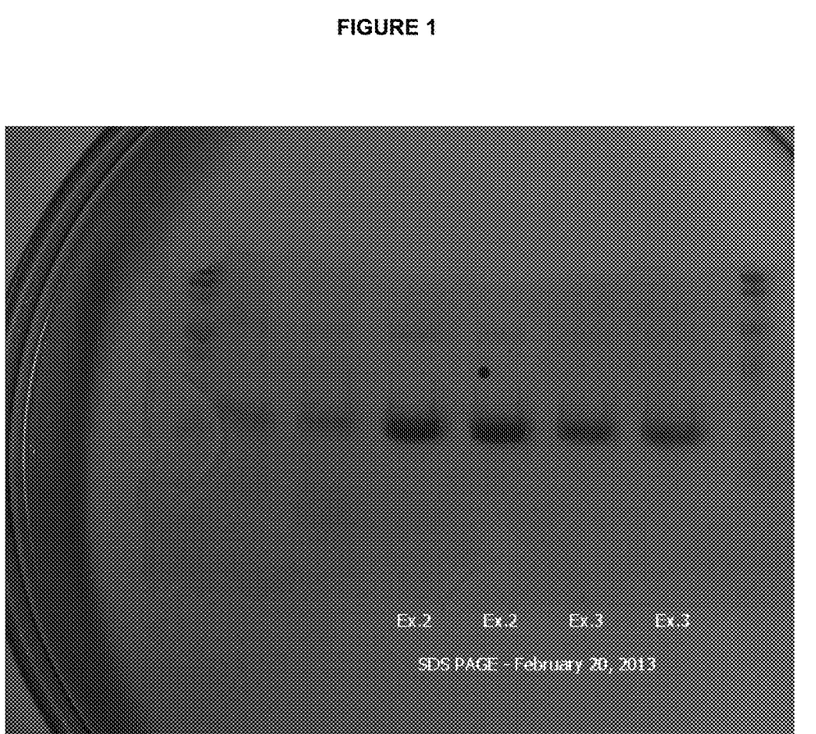
FIG. 1: a photograph of a SDS PAGE electrophoresis of globin prepared from a blood clot.
Figure 2:
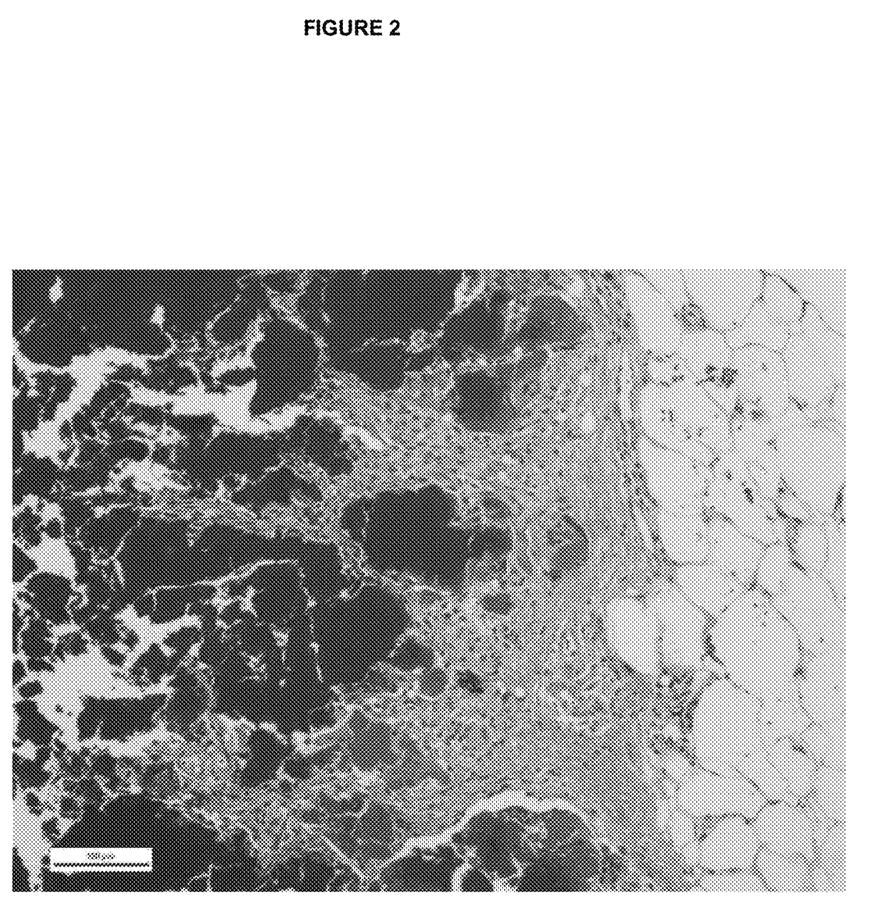
FIG. 2: Photomicrograph n°1. At the hypodermis interface, there were active signs of fibroplasia of moderate grade with infiltrating phagocytes (macrophages and giant cells) and fibroblasts cells of slight grade. (Masson's Trichrome staining, Globin becomes red).
Figure 3:
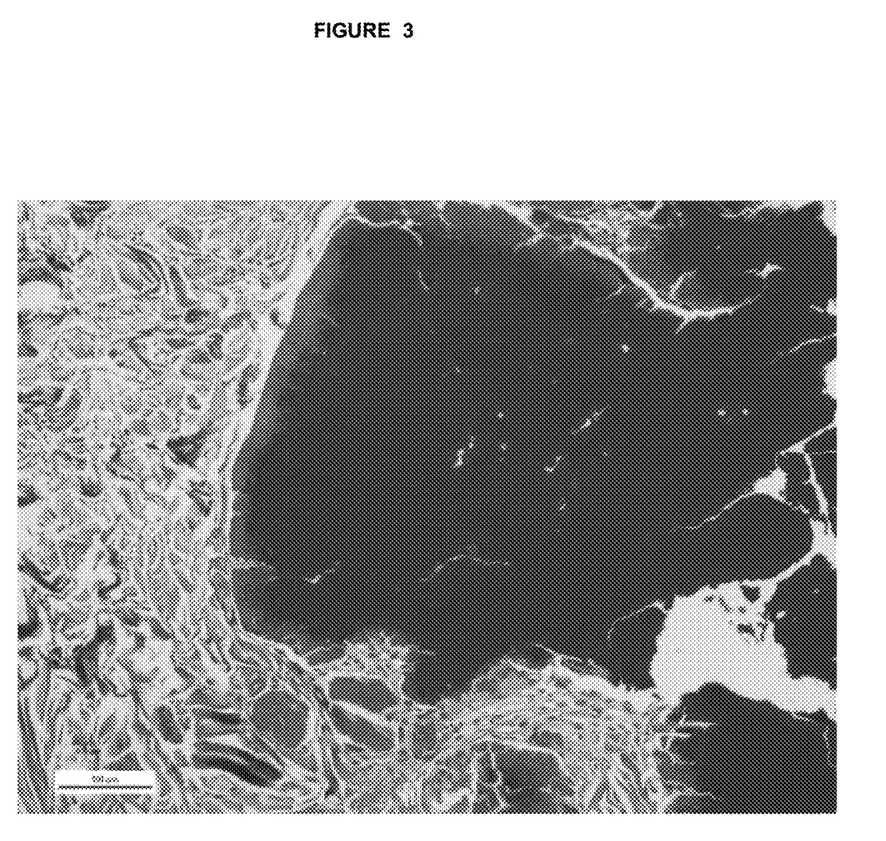
FIG. 3: Photomicrograph n°2. There were areas of the article material in direct contact with the native dermal collagen showing absence of tissue response. This last feature translated a perfect local tolerance of the article. (Masson's Trichrome staining, Globin becomes red).
Figure 4:
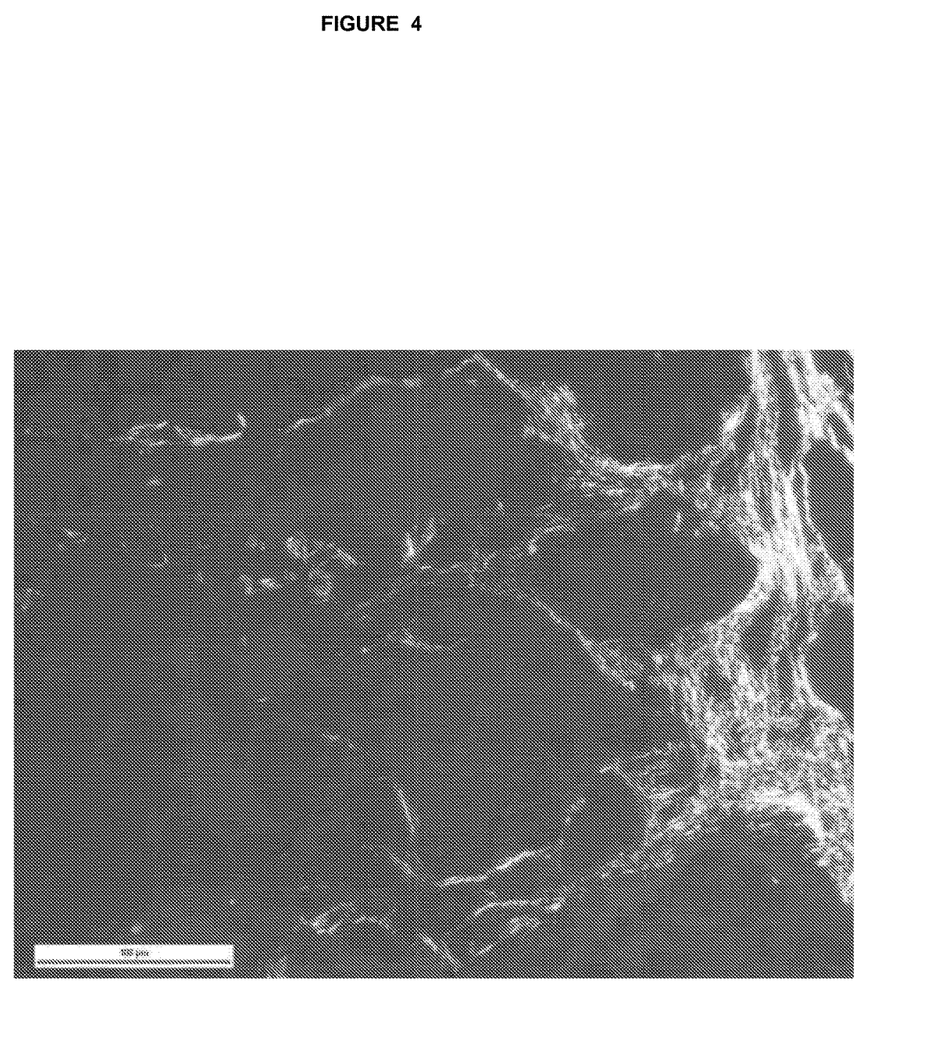
FIG. 4: Photomicrograph n°3. Collagen deposits were noted within the material with signs of collagen type III and predominant collagen type I deposits. No evidence of fibrosis was noted at this stage. (Picrosirius Red staining for histomorphometric quantification of the collagen matrix)
Figure 5:
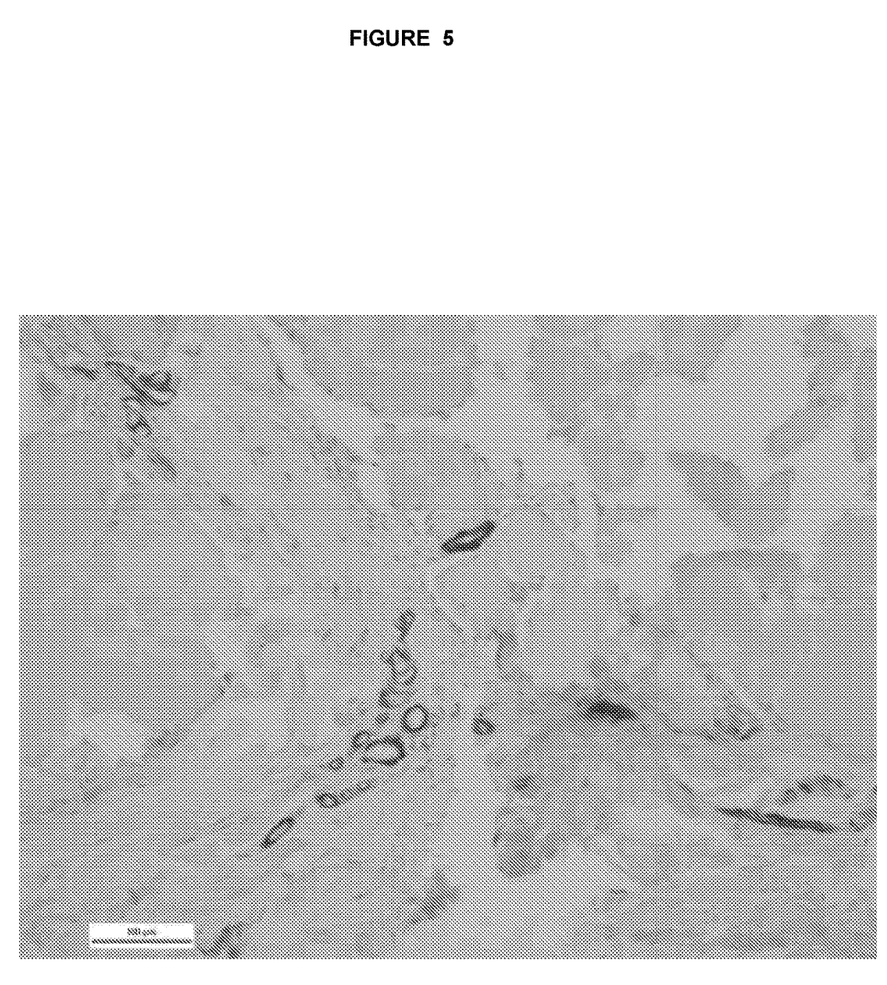
FIG. 5: Photomicrograph n°4. Neovessels of moderate grade were formed within the newly formed tissue surrounding and growing within the article. (Staining of alpha Smooth Muscle Actin, a vascular marker).

Finally the insoluble globin paste is also washed by acetone to remove its water content and then dried by an air flow or under vacuum to prepare a neutral insoluble globin powder. The globin powder weighs 2.15 grams and is distributed in 5 mL luer syringes (500 mg per syringe). The residual quantity of powder is used to test its sterility by inoculation into a culture medium. This powder may be directly sterile if prepared under a sterile laminar air flow. If necessary, the insoluble globin powder may be sterilized by beta or gamma irradiation at a dose of 5 to 30 kGray. The purity of the globin powders prepared by examples 2 and 3 was compared by SDS PAGE electrophoresis. Both preparations give the same profile, showing the 16 kd monomers, some 32 kd dimers and no visible impurities (see photo 1). Surprisingly, we may conclude that despite the fact that globin of example 3 was prepared from a blood clot, its purity was equal to the purity of the globin of example 2 prepared from a more purified hemoglobin solution.

EXAMPLE 4: MIXING THE AUTOLOGOUS SERUM AND THE AUTOLOGOUS GLOBIN POWDER FROM THE SAME PATIENT TO PREPARE THE FINAL "SEROGLOBIN" PASTE

It is preferred, when mixing a powder with a liquid to evacuate the air contained in the powder. If there is some pressurized air incorporated within the paste, it may create spontaneous evacuation of the paste when opening the syringe, creating difficulties for adapting the needle and making the sterile injection impossible or at least questionable. A sterile three way luer stopcock (Cole Parmer reference: #S-31200-80) may be used to evacuate the air from the powder. A standard stopcock may also be used with the same sequence of operations. The three ways stopcock allows to manually connect two ways and to close the third one in the three possible combinations. One 5 mL syringe of examples 2 or 3, containing 500 mg of globin powder is linked to the luer adaptor of one way of the stopcock, under a sterile laminar air flow. The serum containing syringe is linked to the opposite channel and any air bubble in the stopcock is eliminated by evacuating one drop of serum through the perpendicular channel. One 30 mL sterile empty syringe is linked to the perpendicular channel. The evacuation of the air contained in the powder syringe is made possible by pulling the piston of the 30 mL syringe which creates a satisfactory vacuum around the powder particles. The connection is then immediately established between the powder and the serum. The serum is aspirated in the powder and fills all the space visible under the piston. No pressurized air is introduced in the syringe. All the globin paste remains in the syringe when it is opened. The luer connection remains clean, without exit of material from the syringe. The paste may then be reconstituted and homogenized after direct connection of the syringe containing the residual serum and of the syringe containing the powder. The homogenization of the resulting paste is done by 10 transfers of the content of one syringe in the other, back and forth. Then a small bore (0.2 mm) connector enables us to check that the final paste is easily injectable through very thin 30 g hypodermic needles.

The same volume of serum or physiological saline was tested for mixing with 500 mg of powder. With 2.5 mL of serum, the final concentration of globin in the paste was 16.7% w/w (500 mg/2500 mg+500 mg). Its injection through a 30 g needle was followed with a dynamometer. The pressure needed for injection of the paste was constant and less than 25 newtons. With the same volume of saline: 2.5 mL, the resulting paste was difficult to homogenize and was not injectable through a 30 g needle. The addition of 3.5 mL of saline (instead of 2.5 mL) to 500 mg of globin powder gave a 12.5% w/w (500 mg/3500 mg+500 mg) concentration of globin in the paste. In this case, the pressure recorded for injection through a 30 g needle was satisfactory and less than 25 newtons.

The serum and globin mixture of all 5 mL syringes of the batch are gathered in a 20 mL syringe. The global paste is homogenized and then distributed in 1 mL BD syringes (0.8 mL per syringe) which are stored frozen at −20° C., until injection to the patient. A mean of 16 identical syringes of "seroglobin" may be prepared either from a 40 mL blood sample as in example 2, or from only one 20 mL coagulated blood sample as in example 3. After thawing of 1 mL syringes at room temperature, the seroglobin paste is still injectable in the same conditions as the initial paste. Apart the spontaneous thawing of the syringes, no intermediate operation, is requested from the doctor.

EXAMPLE 5: PREFERRED SEQUENCE OF THE OPERATIONS TO PREPARE SYRINGES OF AUTOLOGOUS "SEROGLOBIN" AND ITS MEDICAL APPLICATIONS

The patient is advised by the doctor to donate 20 mL of autologous blood in a specific diagnostic laboratory.

The blood is drawn into dry tubes without anticoagulant agent, specifically labelled, incubated for 30 minutes at room temperature and sent in a package refrigerated at +4° C., to a specific manufacturing laboratory. The blood tubes may be stored at +4° C. for one or two weeks if necessary.

An additional sample of serum is tested for all required viral markers to eliminate the corresponding blood samples and propose another alternative to the patient.

The coagulated blood is preferably processed according to the examples 1 and 3.

The autologous globin powder and autologous serum prepared from 20 mL of coagulated blood are then mixed according to the example 4 to prepare about 16 syringes containing 0.8 mL of paste per syringe. The concentration of globin in the paste may vary from 12 to 20% (w/w).

All syringes from one patient are individually labelled, packaged in labelled sterile pouches which are gathered in a large labelled pouch. The whole lot is then frozen at −20° C., for a maximum of five years. One syringe of each lot is controlled for sterility.

The syringes inventory is accessible to each patient and his doctor through a secure and personal internet access.

Upon request of the doctor, the right number of syringes is shipped at +4° C. and should be injected within few days (less than one week at +4° C.)

Similar syringes can be made by mixing globin powder from an unrelated blood donor with the autologous serum from the patient to be treated.

The main indications of seroglobin are the correction of skin folds and wrinkles by repeated injections, the augmentation of soft tissues like lips, cheeks, breast, muscles, and the healing of acute and chronic wounds.

The seroglobin can be mixed with cells like fibroblasts, keratinocytes, chondrocytes, osteoblasts, adipocytes, stem cells, tissular extracts like adipose tissue from liposuction, or bone fragments to improve their survival before and after implantation.

EXAMPLE 6: IN VIVO DEMONSTRATION OF THE REGENERATIVE PROPERTIES OF THE AUTOLOGOUS SEROGLOBIN INTRADERMAL IMPLANT IN THE SAME HUMAN DONOR 2 grams of autologous globin powder were mixed with 10 mL of autologous serum, both prepared from 20 mL of coagulated blood according to the example 4. The final volume of autologous seroglobin paste was 14 mL. Samples were used for the quality controls of sterility and injectability. The 14 residual BD Luer Lok 1 mL syringes, each containing 0.8 mL of paste per syringe, were stored frozen at −20° C., on Mar. 26, 2013. The globin concentration of the paste was 16.6% (w/w). One syringe of this lot was left at room temperature for 30 mn. Three injections with this syringe, each of 0.2 mL, were performed intradermally with a 30 g needle, on the upper part of the left arm of the subject. Series of photographs were taken immediately and after 1, 2, 3, 7, 16, 23, 30, 40, 51 and 58 days. A first biopsy was taken by a surgeon after 30 days. A second biopsy was taken after 58 days. The two biopsies were received by the subcontracting specialized company in 10% (w/v) neutral buffered formalin solution, 24 hours following sampling. Macrophotographs were performed before preparation. After fixation, each individual biopsy was longitudinally cut in two equal parts. The two biopsy parts were dehydrated in alcohol solutions of increasing concentration, cleared in xylene and embedded in paraffin blocks. One of the block was stored for further analysis and the other one was microtomed (5 μm section thickness+/−0.5 μm). Four serial sections were prepared using a microtome (MICROM®, France):

One section was stained with Masson's Trichrome for general morphology and extracellular matrix evaluation.

One section was stained with Safranin-Hematoxylin-Eosin for analysis of the inflammatory reaction.

One section was stained with Picrosirius Red for histomorphometric quantification of the collagen matrix.

One section was used for the immunohistochemistry (IHC) determination of the alpha-SMA vascular marker.

The sections were evaluated using a Nikon Eclipse 80i microscope fitted with ×2, ×10, ×20 and ×40 objectives coupled with a digital camera Nikon. A semi-quantitative evaluation of the local effects was performed using a 0-4 grading scale, involving evaluation of the inflammatory reaction (polymorphonuclear cells PMNs, lymphocytes, plasma cells, macrophages and giant cells/osteoclasts), fibrin, necrosis, neovessels, degradation and material debris.

Photomicrographs were taken of the areas of interest. Digitization of the whole sections was also performed.

The sections were evaluated using a color images analyzing system. The histomorphometric regions of interest included the implant material and the new collagen matrix formed around and within each material residue. Quantitative histomorphometric analysis was performed to determine the amount of residual implant surface area, the total of collagen content and the ratio collagen I/collagen III.

The following paragraph is a copy taken from the official report of the tests carried out by this independent company.

""""The skin biopsy taken after two months of implantation showed a massive presence of the test article fragmented in three closed portions, well integrated into the surrounding intradermal tissue. One of the material portions was placed at the hypodermis interface. At the hypodermis interface, there were active signs of fibroplasia of moderate grade with infiltrating phagocytes (macrophages and giant cells) and fibroblasts cells of slight grade (photomicrograph n°1). The remaining surface of the article material showed similar tissue response at a slightly lower extent. The signs of remodelling were more intense at the hypodermis interface. There were areas of the article material in direct contact with the native dermal collagen showing absence of tissue response (photomicrograph n°2). This last feature translated a perfect local tolerance of the article. Collagen deposits were noted within the material with signs of collagen type III and predominant collagen type I deposits (photomicrograph n°3). No evidence of fibrosis was noted at this stage. Neovessels of moderate grade were formed within the newly formed tissue surrounding and growing within the article (photomicrograph n°4).

To our knowledge and contrary to the seroglobin material herein characterized, no other material was ever described to be so well tolerated, without any inflammatory reaction and capable at the same time to induce local tissue regeneration by cell migration and colonization.

EXAMPLE 7: MAIN THERAPEUTIC INDICATIONS FOR USE OF THE SEROGLOBIN MIXTURE

This new preparation is a preparation for use, preferably by injection, in a therapeutic method of regenerating tissue, including for filling wrinkles, or other cutaneous flaws, for the augmentation of lips, cheeks, or other body parts, alone or in association or mixture with other augmentation materials, and/or for augmentation of tissues, including deficient sphincters, vocal cords, periodontal tissues. It may also be used for healing of internal surgical wounds, of parts of organs, of chronic wounds of cutaneous tissues, including in diabetic patients or patients affected by arterial or venous disorders which create poor local vascularization of the limbs, or in patients affected by scars, and/or for aiding the regeneration of a granulation tissue on deep burn wounds after excision of the necrotic tissues. For wound care, the seroglobin may be used directly as a powder, or as a paste, or in association with sheets, textiles, porous or not. It may also be used in association with porous meshes. All the associated materials should preferably be bioresorbable to avoid taking them off from the wound, if necessary, after its partial or complete healing.

BIBLIOGRAPHY

1. Araki J., Jona M., Eto H., Aoi N., Kato H., Suga H., Doi K., Yatomi Y., Yoshimura K. (2012)
Optimized preparation method of platelet-concentrated plasma and noncoagulating platelet-derived factor concentrates: Maximization of platelet concentration and removal of fibrinogen. Tissue Eng Part C Methods, March 18 (3) 176-185
2. Flatow F. A. Jr. and Freireich E. J. (1966)
The increased effectiveness of platelet concentrates prepared in acidified plasma. Blood 27, 449.
3. Boldt J., von Bormann B., Kling D., Jacobi M., Moosdorf R. and Hempelmann G. (1990)
Preoperative plasmapheresis in patients undergoing cardiac surgery procedures. Anesthesiology, 72, 282.
4. Weibrich G., Kleis W. K., Hafner G. and Hitzler W. E. (2002)
Growth factor levels in platelet-rich plasma and correlations with donor age, sex, and platelet count. J Cranio Maxillofac Surg 30, 97.
5. Eppley B. L., Woodell J. E., and Higgins J. (2004)
Platelet quantification and growth factor analysis from platelet-rich plasma: implications for wound healing. Plast Reconstr Surg 114, 1502.
6. Aiba-Kojima E., Tsuno N. H., Inoue K., Matsumoto D., Shigeura T., Sato T., Suga H., Kato H., Nagase T., Gonda K., Koshima I., Takahashi K. and Yoshimura K. (2007)
Characterization of wound drainage fluids as a source of soluble factors associated with wound healing: comparison with platelet-rich plasma and potential use in cell culture. Wound Repair Regen 15, 511.
7. Gnecchi M., Zhang Z., Ni A. and Dzau V. J. (2008)
Paracrine mechanisms in adult stem cell signaling and therapy. Circ Res 103, 1204.
8. Mimeault M. and Batra S. K. (2010)
Recent advances on skin resident stem/progenitor cell functions in skin regeneration, aging and cancers and novel anti-aging and cancer therapies. J Cell Mol Med 14, 116.
9. Lucarelli E., Beccheroni A., Donati D., Sangiorgi L., Cenacchi A., Del Vento A. M., Meotti C., Bertoja A. Z., Giardino R., Fornasari P. M., Mercuri M. and Picci, P. (2003)
Platelet-derived growth factors enhance proliferation of human stromal stem cells. Biomaterials, 24, 3095.
10. Anitua E., Andia I., Ardanza B., Nurden P. and Nurden A. T. (2004) Autologous platelets as a source of proteins for healing and tissue regeneration. Thromb Haemost 91, 4.
11. Niemeyer P., Fechner K., Milz S., Richter W., Suedkamp N. P., Mehlhorn A. T., Pearce S. and Kasten P. (2010)
Comparison of mesenchymal stem cells from bone marrow and adipose tissue for bone regeneration in a critical size defect of the sheep tibia and the influence of platelet-rich plasma. Biomaterials, 31, 3572.
12. Marx R. E., Carlson E. R., Eichstaedt R. M., Schimmele S. R., Strauss J. E. and Georgeff K. R. (1998)
Platelet-rich plasma: growth factor enhancement for bone grafts. Oral Surg Oral Med Oral Pathol Oral Radiol Endod 85, 638.
13. Khalafi R. S., Bradford D. W. and Wilson M. G. (2008)
Topical application of autologous blood products during surgical closure following a coronary artery bypass graft. Eur. J. Cardiothorac Surg 34, 360.
14. Alio J. L., Abad M., Artola A., Rodriguez-Prats J. L., Pastor S. and Ruiz-Colecha J. (2007)
Use of autologous platelet-rich plasma in the treatment of dormant corneal ulcers. Ophthalmology, 114, 1286.
15. Nikolidakis D. and Jansen J. A. (2008)

The biology of platelet-rich plasma and its application in oral surgery: literature review. Tissue Eng Part B Rev 14, 249.
16. Savarino L., Cenni E., Tarabusi C., Dallari D., Stagni C., Cenacchi A., Fornasari P. M., Giunti A. and Baldini N. (2006)
Evaluation of bone healing enhancement by lyophilized bone grafts supplemented with platelet gel: a standardized methodology in patients with tibial osteotomy for genu varus. J Biomed Mater Res B Appl Biomater 76, 364.
17. Eppley B. L., Pietrzak W. S. and Blanton M. (2006)
Platelet-rich plasma: a review of biology and applications in plastic surgery. Plast Reconstr Surg 118, 147.
18. Pallua N., Wolter T. and Markowicz M. (2010)
Platelet-rich plasma in burns. Burns 36, 4.
19. Foster T. E., Puskas B. L., Mandelbaum B. R., Gerhardt M. B. and Rodeo S. A. (2009)
Platelet-rich plasma: from basic science to clinical applications. Am J Sports Med 37, 2259.
20. Anitua E., Sanchez M., Nurden A. T., Nurden P., Orive G. and Andia I. (2006)
New insights into and novel applications for platelet-rich fibrin therapies. Trends Biotechnol 24, 227.
21. Man D., Plosker H. and Winland-Brown J. E. (2001)
The use of autologous platelet-rich plasma (platelet gel) and autologous platelet-poor plasma (fibrin glue) in cosmetic surgery. Plast Reconstr Surg 107, 229.
22. Freymiller E. G. and Aghaloo T. L. (2004)
Platelet-rich plasma: ready or not? J Oral Maxillofac Surg 62, 484.
23. Coombes B. K., Bisset L. and Vicenzino B. (2010)
Efficacy and safety of corticosteroid injections and other injections for management of tendinopathy: a systematic review of randomised controlled trials. Lancet 376, 1751.
24. Dohan Ehrenfest D. M., Rasmusson L. and Albrektsson T. (2009)
Classification of platelet concentrates: from pure platelet-rich plasma (P-PRP) to leucocyte- and platelet-rich fibrin (L-PRF). Trends Biotechnol 27, 158.
25. Anitua E., Sanchez M., Orive G, and Andia I. (2007)
The potential impact of the preparation rich in growth factors (PRGF) in different medical fields. Biomaterials 28, 4551.
26. Sclafani A. P., Mc Cormick S. A.: (2011)
Induction of dermal collagenesis, angiogenesis and adipogenesis in human skin by injection of platelet-rich fibrin matrix. Arch. Facial Plast. Surg. October 17: (www.arch-facial.com)
27. Hom D. B., Linzie B. M., Huang T. C. (2007)
The healing effects of autologous platelet gel on acute human skin wounds. Arch Facial Plast Surg. 9(3):174-183.
28. Sclafani A. P., Romo T. R. III, Ukrainsky G. et al. (2005)
Modulation of wound response and soft tissue ingrowth in synthetic and allogeneic implants with platelet concentrate. Arch Facial Plast Surg. 7(3):163-169.
29. Catelas I., Dwyer J. F. and Helgerson S. (2008)
Controlled release of bioactive transforming growth factor beta-1 from fibrin gels in vitro. Tissue Eng Part C Methods 14, 119.
30. Hoben G., Schmidt V. J., Bannasch H. and Horch R. E. (2011)
Tissue augmentation with fibrin sealant and cultured fibroblasts: a preliminary study. Aesthetic Plast. Surg. December; 35 (6): 1009-1015
31. Ayache S., Panelli M. C., Byrne K. M., Slezak S., Leitman S. F., Marincola F. M. and Stroncek D. F. (2006)
Comparison of proteomic profiles of serum, plasma, and modified media supplements used for cell culture and expansion. Journal of Translational Medicine, October 4, 4-40
32. Fernandez-Cossio S., Castano-Oreja M. T. (2006)
Biocompatibility of two novel dermal fillers: Histological evaluation of a hyaluronic acid filler and a polyacrylamide filler. Plastic and reconstructive surgery, 117, 1789-1796

The invention claimed is:

1. A method for preparing a paste containing 14 to 20% per weight of globin and being injectable through a thin 30 g hypodermic needle for regenerating tissues or healing wounds, which can be administered to a patient, consisting of:
   a) obtaining a whole blood without any anticoagulant agent from a patient,
   b) allowing said whole blood sample to clot,
   c) separating the obtained serum from said clot,
   d) obtaining, from erythrocytes of a blood sample of said patient, after their separation from the plasma or the serum of said sample, an autologous preparation of globin being insoluble at physiological pH, and
   e) mixing quantities of said serum and said autologous preparation of globin being insoluble at physiological pH to obtain a paste containing from 14% to 20% per weight of globin and being injectable through a thin 30 g hypodermic needle.

2. The method according to claim 1 wherein said obtained serum and said globin are obtained from the same blood sample of said patient.

3. The method according to claim 1 wherein the paste contains from 15 to 20% per weight of globin.

4. A method for preparing a preparation for regenerating tissues or healing wounds, which can be administered to a patient, consisting of obtaining a whole blood without any anticoagulant agent from a patient,
   a) allowing said whole blood sample to clot;
   b) separating the obtained serum from said clot;
   c) obtaining, from erythrocytes of a blood sample of said patient, after their separation from the plasma or the serum of said sample, an autologous preparation of globin being insoluble at physiological pH;
   d) mixing said serum and said preparation containing globin being insoluble at physiological pH, to obtain a paste containing at least 14% per weight of globin, wherein said paste is injectable through a thin 30 g hypodermic needle;
   and e) mixing said paste with a tissue augmentation material being cross-linked hyaluronic acid.

5. A method for preparing a preparation for regenerating tissues or healing wounds, which can be administered to a patient, consisting of:
   a) obtaining a whole blood without any anticoagulant agent from a patient;
   b) allowing said whole blood sample to clot;
   c) separating the obtained serum from said clot;
   d) obtaining, from erythrocytes of a blood sample of said patient, after their separation from the plasma or the serum of said sample, an autologous preparation of globin being insoluble at physiological pH;
   e) mixing quantities of said serum and of said preparation containing globin being insoluble at physiological pH to obtain a paste containing from 14% to 20% per weight of globin, wherein said paste is injectable through a thin 30 g hypodermic needle; and
   f) mixing said paste with a component selected from the group consisting of a tissue filling or augmentation material, a wound healing agent, an adhesive agent selected from the group consisting of synthetic or natural adhesive polymeric agents, hemoglobin and a cell growth factor.

6. A method for preparing a preparation for regenerating tissues or healing wounds which can be administered to a patient, consisting of;
   a) obtaining a whole blood without any anticoagulant agent from a patient,
   b) allowing said whole blood sample to clot,
   c) separating the obtained serum from said clot, and
   d) mixing quantities of said serum and of a preparation containing homologous globin being insoluble at physiological pH to obtain a paste containing from 14% to 20% per weight of globin, wherein said paste is injectable through a thin 30 g hypodermic needle.

\* \* \* \* \*